US005371248A

United States Patent [19]
Rudnick

[11] Patent Number: 5,371,248
[45] Date of Patent: Dec. 6, 1994

[54] ALKYLATED BENZOFURAN-DERIVED LUBRICANTS

[75] Inventor: Leslie R. Rudnick, Lawrenceville, N.J.

[73] Assignee: Mobil Oil Corporation, Fairfax, Va.

[21] Appl. No.: 20,487

[22] Filed: Feb. 22, 1993

Related U.S. Application Data

[63] Continuation-in-part of Ser. No. 748,731, Aug. 22, 1991, abandoned.

[51] Int. Cl.$^5$ .............. C07D 307/91; C10M 105/08; C10M 129/02; C10M 129/86
[52] U.S. Cl. ................... 549/460; 549/218; 549/222; 252/52 R
[58] Field of Search .......... 252/52 R; 549/460, 218, 549/222

[56] References Cited

U.S. PATENT DOCUMENTS

| | | | |
|---|---|---|---|
| 2,128,109 | 8/1938 | Wiezevich | 252/52 R |
| 2,500,732 | 3/1950 | Abbott | 549/460 |
| 4,891,448 | 1/1990 | Garces et al. | 585/452 |
| 5,171,915 | 12/1992 | Forbus et al. | 585/455 |

*Primary Examiner*—Jerry D. Johnson
*Attorney, Agent, or Firm*—A. J. McKillop; M. D. Keen

[57] ABSTRACT

Monoalkylated benzofuran adducts provide high temperature stable lubricant fluids having not only excellent thermal stability, but good low-temperature properties and excellent additive solubility as well.

7 Claims, 1 Drawing Sheet

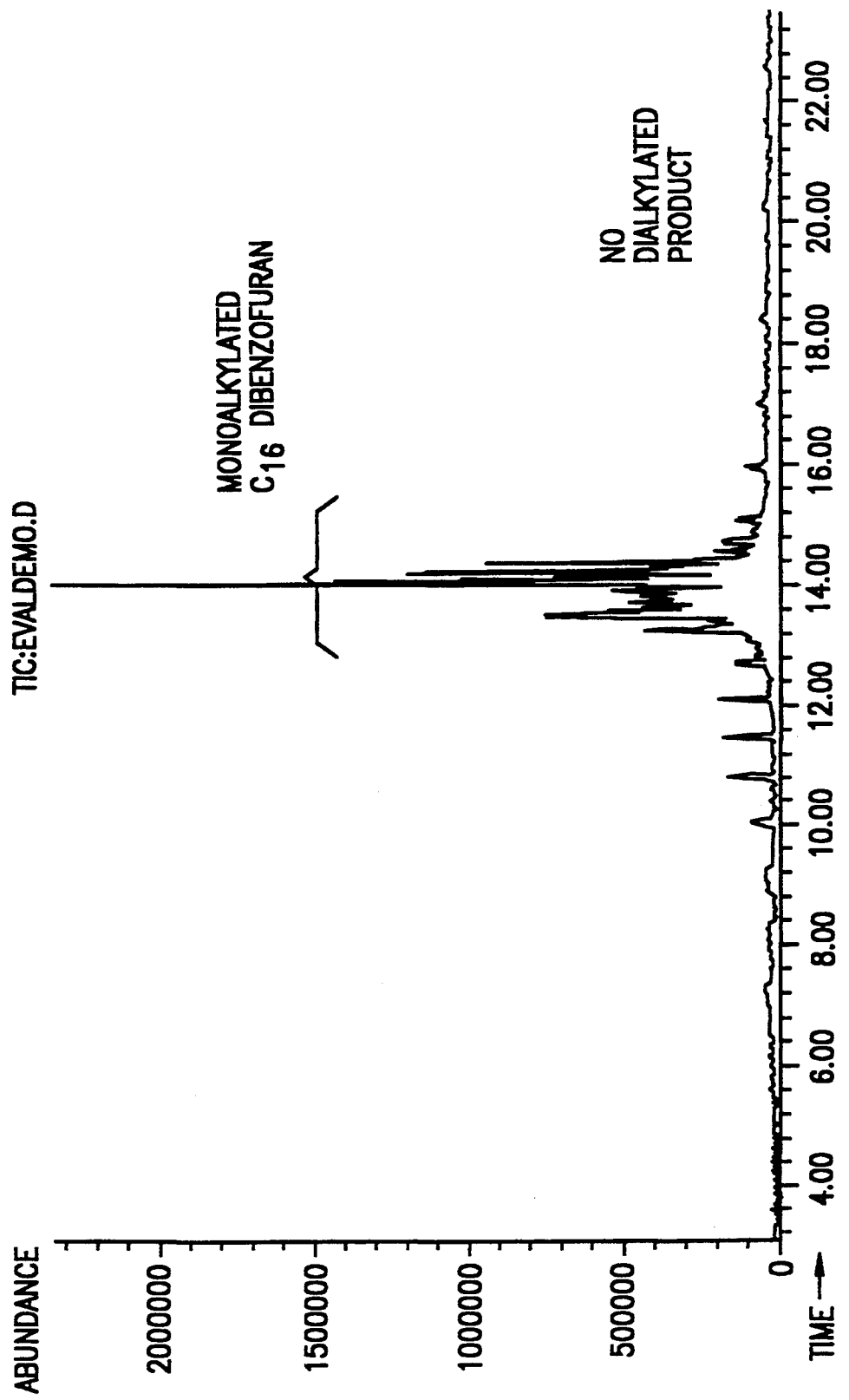

ALKYLATED BENZOFURAN-DERIVED LUBRICANTS

CROSS REFERENCE TO RELATED APPLICATIONS

This application is a continuation-in-part of Ser. No. 07/748,731 filed Aug. 22, 1991 now abandoned.

BACKGROUND OF THE INVENTION

1. Field of the Invention

This invention is directed to improved lubricant compositions comprising monoalkylated dibenzofurans alone or in combination with synthetic or mineral oil fluids, and to mineral or synthetic lubricant compositions or hydrocarbyl or hydrocarbyloxy fuels containing minor amounts of said dibenzofurans as multifunctional additives therefor.

2. Description of Related Art

Polyphenyl ethers are known and have been used as lubricants in special applications. Polyphenyl ethers suffer from very high cost due to difficult synthesis and have poor low-temperature properties.

Incorporation of linear alkyl groups into diphenyl ether eliminates both of the above problems and provides a novel, relatively inexpensive lubricant having excellent low-temperature properties. The use of these adducts as a lubricant or lubricant additive in either mineral or synthetic lubricants has been recently disclosed.

Dibenzofuran has previously been used as an insecticide & we now disclose the preparation and use of alkylated dibenzofurans as a new class of lubricating fluids and lubricant and fuel additives. These monoalkylated benzofurans have the advantages of alkylated diphenyl ethers in that the polar oxygen provides excellent additive solubility and good lubricating properties.

Garces, U.S. Pat. No. 4,891,448 is directed to the alkylation of polycyclic aromatics over natural zeolites such as mordenite, offretite and gmelinite.

Abbott, Jr., U.S. Pat. No. 2,500,732 is directed to a method of preparing monoethyldibenzofuran in the presence of a Friedel-Crafts type catalyst.

Wiezovich, U.S. Pat. No. 2,128,109 is directed to high molecular weight oils or blending agents and more particularly to condensation products of oxygenated aromatics such as diphenyl oxide and the like prepared in the presence of materials such a aluminum chloride.

To the best of Applicants knowledge and belief the herein described monoalkylated benzofuran-derived adducts have not been used previously as functional lubricant fluids or additives therefor.

BRIEF SUMMARY OF THE INVENTION

This application is directed to novel lubricant compositions comprising from about less than one percent to about 100% of monoalkylated dibenzofurans as disclosed herein and to mineral and synthetic lubricants and fuels containing minor proportions of the disclosed dibenzofurans as multifunctional additives.

The principal limitation of getting monoalkylated fluids of diphenyl ether using octadecene or lower olefins having greater than 5 cSt viscosity at 100° C. limits end use applications. Alkylation of dibenzofuran with hexadecene provides a monoalkylated adduct having a viscosity of >7 cSt. This opens a wider range of application areas for this novel lubricating fluid.

The products obtained from the reaction of a linear olefin and dibenzofuran in the presence of specific zeolite catalysts are unique not only in composition and structure but in utility. Part of the uniqueness may be derived from the specific reaction over zeolite catalysts; generally, they have a higher VI at a given viscosity. The incorporation of various alkyl groups into the dibenzofuran structure provides compositions of different viscosity and low temperature viscometrics.

The thermal stability of these alkylated dibenzofurans is excellent and believed to be improved over materials of branched structure due to the facility for carbon-carbon bond breaking in the latter materials.

These unique lubricants exhibit beneficial properties from the unique reaction of olefin with the dibenzofuran structures in such a way as to remain predominantly linear. This is a direct result of the catalytic reaction. This combination provides for the novel structural class disclosed here. The use of these compositions of matter as either functionalized alkyl benzofurans lubricants fluids or lubricant additives is believed to be novel.

The use of these adducts as a lubricant or lubricant additive in either mineral or synthetic lubricants is unique and provides improved properties and performance benefits due to inherent synergism. It is expected that the performance benefits will include antifatigue, antispalling, antistaining, antisquawking, improved additive solubility, improved load carrying/bearing, extreme pressure, improved thermal and oxidative stability, friction reducing, antiwear, anticorrosion, cleanliness improving, low- and high-temperature antioxidant, demulsifying, emulsifying and detergency properties.

It is therefore an object of this invention to provide novel lubricant compositions comprising the dibenzofurans in accordance with the invention and novel lubricant and fuel compositions containing minor proportions of said dibenzofurans as additives.

BRIEF DESCRIPTION OF THE DRAWING

The FIGURE is a GCMS of monoalkylated product in accordance with the invention.

DESCRIPTION OF THE PREFERRED EMBODIMENTS

Broadly, the novel class of hydrocarbon products of the present invention can be characterized as adducts of hydrocarbyl substituent, and a benzofuran. The hydrocarbyl group can contain from $C_3$-$C_{500}$, preferably $C_6$-$C_{50}$ and most preferably $C_8$-$C_{18}$. The hydrocarbyl group can optionally contain S, N, O, P, and/or F. The hydrocarbyl moiety can be alkyl, alkenyl, alkynyl, arylalkyl, aliphatic, cyclic, linear or branched. Substitution can be on one or more positions of the aromatic rings, with alkylation on either or both rings.

The preparation of these novel compositions is by means of a catalytic addition reaction. The exact mechanism of the reaction is not important to the purposes of this invention, so long as the hydrocarbyl group becomes attached to the dibenzofurans described herein.

The preparation of these novel compositions is by means of a zeolite catalytic addition reaction wherein specific zeolite catalysts are utilized. The zeolite catalysts should be at least partly in the acidic (H) form to provide the acidity for the reaction. The zeolites may contain other cations also, such as ammonium (NH4+). The zeolite is preferably a large pore zeolite such as the faujasites, e.g. zeolites X, Y, USY, UHP-Y, ZSM-12, ZSM-20 or zeolite beta and other large pore type zeolites. Another highly useful zeolite is MCM-22. It is to be noted that zeolite USY is sold commercially as FCC Octacat® USY cracking catalyst. The exact mechanism of the reaction is not important to the purposes of this invention, so long as the hydrocarbyl group becomes attached to the benzofurans described herein.

One preferred method of reaction between the hydrocarbyl group and the dibenzofuran is the combination of these reactants in the presence of specific zeolite catalysts. Non-limiting examples are Octacat USY and MCM-22. Additional catalysts which we believe could be used advantageously in this invention are ZSM-12 and other large-pore and/or relatively large pore zeolites. FCC Octacat USY is described in U.S. Pat. No. 4,898,846 and MCM-22 is described in U.S. Pat. No. 4,983,276. This reaction is affected at temperatures ranging from ambient to 350° C., preferably from 100°-250° C. and most preferably from 180°-240° C. over a period required to produce the desired conversion of reactants to product. Optionally, the reaction can be performed in a batch or semi-batch mode by continuous or partial addition of catalyst or hydrocarbyl substituent to the dibenzofuran.

The catalyst can be used at levels ranging from 1 gram/mole of aromatic to 100 grams/mole of aromatic, preferably from 5 g/mole of aromatic to 50 grams/mole of aromatic, and most preferably from 10–30 grams catalyst/mole of aromatic.

Generally speaking the molar ratio of olefinic alkylating agent to the dibenzofuran varies from about 0.5:1.0 to about 10.0:1.0 and preferably from about 1.0:10 to about 4.0:1.0.

In general, the production of monoalkylated dibenzofuran adducts is favored by the use of specific zeolite catalysts such as zeolite beta or zeolite Y preferably USY, of controlled acidity, preferably with an alpha value below about 200 and, for best results, below 100, e.g., about 25–50. The alkylated product is substantially monoalkylated—see the Drawing wherein the presence of only monoalkylated material is detected. Abundance is the signal strength or intensity of the alkylated product as measured by the number of molecules.

The above preferred method demonstrates the use of the catalysts of choice. MCM-22 is disclosed in U.S. Pat. No. 4,954,325 which is incorporated herein in its entirety by reference. It is also described in U.S. Pat. No. 5,100,534, which is incorporated herein in its entirety by reference, as a crystalline aluminosilicate zeolite. MCM-22 is also described in U.S. Pat. No. 5,103,066 as having a CI (constraint index) of 1.5 at 454° C. U.S. Pat. No. 5,103,066 is incorporated herein by reference.

Constraint Index (CI) values for some typical zeolites are given below.

|  | CI (at test temperature) |
| --- | --- |
| ZSM-5 | 6–8.3 (371° C.–316° C.) |
| ZSM-22 | 7.3 (427° C.) |
| MCM-22 | 1.5 (454° C.) |
| Dealuminized Y | 0.5 (510° C.) |

The method by which Constraint Index of acidic zeolites is determined is described fully in U.S. Pat. No. 4,016,218 incorporated herein by reference for details of the method. The above-described CI is a highly important definition of the zeolites which are useful in the process of the present invention.

FCC (fluid catalytic cracking) catalysts based on ultrastable Y type (USY) zeolites are well known in the art to make gasoline having a higher octane number than FCC catalysts based on rare earth exchanged Y (REY) or calcined rare earth exchanged Y (CREY); see U.S. Pat. No. 5,102,530 which is incorporated herein by reference. It is further disclosed in U.S. publication/notice H 449 (Mar. 1, 1988) to Rudesill that the commercially available FCC cracking catalyst (Octacat) comprises about 40% Ultrastable Type Y zeolite combined with a silica-alumina sol binder and kaolin matrix and that preferably the USY containing Octacat may comprise from about 15 to about 60 wt % USY and more preferably from about 35 to about 45 wt % USY. H 449, filed Jul. 3, 1987 and published Mar. 1, 1988 to Rudesill is incoporated herein by reference.

In general, the production of monoalkylated dibenzofurans is favored by the use of above-recited zeolite catalysts such as zeolite beta or zeolite Y, preferably USY, of controlled acidity, preferably with an alpha value below about 200 and, for best results, below 100, e.g., about 25–50.

The alpha value of the zeolite is an approximate indication of the catalytic cracking activity of the catalyst compared to a standard catalyst. The alpha test gives the relative rate constant (rate of normal hexane conversion per volume of catalyst per unit time) of the test catalyst relative to the standard catalyst which is taken as an alpha of 1 (Rate Constant +0.016 sec −1). The alpha test is described in U.S. Pat. No. 3,354,078 and in J. Catalysis, 4,527 (1965); 6,278 (1966); and 61, 395 (1980), to which reference is made for a description of the test. The experimental conditions of the test used to determine the alpha values referred to in this specification include a constant temperature of 538° C. and a variable flow rate as described in detail in J. Catalysis, 61, 395 (1980).

One preferred method of reaction between the hydrocarbyl group and the dibenzofuran is the combination of these reactants in the presence of the specific zeolite catalysts affected at temperatures ranging from ambient to 350° C., preferably from 100°-250° C. and most preferably from 180°-240° C. over a period required to produce desired conversion of reactants to product. Optionally, the reaction can be performed in a batch or semibatch mode by continuous or partial addition of the catalyst or hydrocarbyl group to the dibenzofuran.

The monoalkylated dibenzofurans produced by this process may be represented generally by the structure:

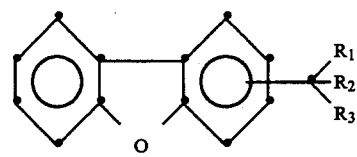

Where $R_1$, $R_2$ or $R_3$ may be H, alkyl, alkenyl, alkynyl, aryl, alkylaryl, cyclic linear or branched as previously described; and/or where $R_1$, $R_2$, and/or $R_3$ can contain S, N, O, P and/or F; and/or where $R_1$, $R_2$ and/or $R_3$ are linked to form a cyclic structure.

The hydrocarbon compositions of the present invention relate to improved thermally and oxidatively stable fluids. These may be used optionally as liquid lubricants or in liquid lubricant compositions, and as solid lubricants or in solid lubricant compositions including greases, such as polyurea, lithium carboxylate or clay-thickened greases.

These hydrocarbon compositions may also be used in combination with known additives, for example, antioxidants, EP/antiwear agents, inhibitors, detergents and dispersants, and viscosity index improvers. Non-limiting examples of antioxidant include phenols which can be hindered and aromatic amines.

Non-limiting examples of EP/antiwear additives include zinc phosphorodithioates, sulfurized esters, sulfurized olefins, phosphonates, phosphates, phosphorothionates, etc. Non-limiting examples of inhibitors include DMTD, phenothiazine, etc. Non-limiting examples of detergents and dispersants include sulfonates, phenates, and polymeric succinimides. These can be either metallic or non-metallic. Metallic detergents can be calcium or magnesium derived and can be neutral or over based.

The hydrocarbon compositions of this invention can be used alone or in combination with other synthetic and/or mineral oil fluids.

Fuel compositions are also contemplated for use herein, these include both hydrocarbon fuels, including gasoline, naphtha and diesel fuels or alcoholic fuels or mixtures of alcoholic and hydrocarbon fuels. Fuel compositions can contain 10 to 1000 pounds of the benzofurans as additive per 1000 barrels of fuel or more preferably 25 to 250 pounds per 1000 barrels of fuel.

When the compositions of the present invention are used alone or in combination with other synthetic and/or mineral oil fluids, the below described oils of lubricating viscosity may be used.

In general, mineral oils, both paraffinic, naphthenic and mixtures thereof, employed as the lubricant, or grease vehicle, may be of any suitable lubricating viscosity range, as for example, from about 45 SSU at 100° F. to about 6000 SSU at 100° F. to about 6000 SSU at 100° F. and preferably, from about 50 to about 250 SSU at 210° F. These oils may have viscosity indexes ranging to about 95 are preferred. The average molecular weights of these oils may range from about 250 to about 800. Where the lubricant is to be employed in the form of a grease, the lubricating oil is generally employed in an amount sufficient to balance the total grease composition, after accounting for the desired quantity of the thickening agent, and other additive components to be included in the grease formulation.

A wide variety of materials may be employed as thickening or gelling agents. These may include any of the conventional metal salts or soaps, which are dispersed in the lubricating vehicle in grease-forming quantities in an amount to impart to the resulting grease composition the desired consistency. Other thickening agents that may be employed in the grease formulation may comprise the non-soap thickeners, such as surface-modified clays and silicas, aryl ureas, calcium complexes and similar materials. In general, grease thickeners may be employed which do not melt and dissolve when used at the required temperature within a particular environment; however, in all other respects, any materials which is normally employed for thickening or gelling hydrocarbon fluids for forming grease can be used in preparing grease in accordance with the present invention.

In instances where synthetic oils, or synthetic oils employed as the lubricant or vehicle for the grease, are desired in preference to mineral oils, or in combination therewith, various compounds of this type may be successfully utilized. Typical synthetic oils include, but are not limited to, polyisobutylene, polybutenes, hydrogenated polydecenes, polypropylene glycol, polyethylene glycol, trimethylpropane esters, neopentyl and pentaerythritol esters, di(2-ethylhexyl) sebacate, di(2-ethylhexyl) adipate, dibutyl phthalate, fluorocarbons, silicate esters, silanes, esters of phosphorus-containing acids, liquid ureas, ferrocene derivatives, hydrogenated synthetic oils, chain-type polyphenyls, siloxanes and silicones (polysiloxanes), alkyl-substituted diphenyl ethers typified by a butyl-substituted bis(p-phenoxy phenyl) ether, phenoxy phenylethers etc.

When used as additives the materials in accordance with the invention have the ability to improve both the thermal and oxidative stability as well as the additive solubility of the oleagenous materials, i.e., synthetic and/or mineral oil fluids or vegetable oils with which they have been blended.

It is to be understood, however, that the prior art additives disclosed herein are used for their known purposes do not detract from the value of the compositions of this invention, rather these materials enhance the beneficial characteristics of the disclosed alkylated dibenzofuran fluids.

Lubricant compositions in accordance with the invention may comprise from less than about 1 to about 100% of the alkylated benzofurans of the invention and/or from less than about 100% to about 1% of a synthetic or mineral oil or vegetable oil of lubricating viscosity or grease prepared therefrom and from about 0.001 to about 20 wt % of additive material based on the total weight of the composition. However, any suitable blending ratio may be used, for example, a blend of 20% monoalkylated dibenzofuran and,for example, 80% PAO has been advantageously used. The majority benzofurans may make up a majority of the blend up to about 80–99 wt %. The present fluid may therefore be used as replacements for, or as components of current lubricant formulations. Ester-containing fluids and/or synthetic polyalphaolefins have been found to be very useful blending agents.

The following examples are exemplary only and are not intended to limit the invention.

EXAMPLE 1

To a vigorously stirred mixture of dibenzofuran (168.2 g, 1.0 mole) and 1-tetradecene (196 g, 1.0 mole) in a flask fitted with thermocouple and reflux condenser was added 15 g of FCC Octacat USY catalyst. The mixture was heated to 200° C. with stirring for six hours. After cooling to room temperature, the mixture was filtered to remove catalyst and vacuum distilled to 170° C. at 0.5–1.5 mm Hg to remove unreacted starting materials.

EXAMPLE 2

Using the procedure in Example 1, dibenzofuran (168.2 g, 1.0 mole) and 1-tetradecene (196 g, 1.0 mole) were reacted using 30 grams of FCC Octacat USY catalyst.

EXAMPLE 3

Using the procedure in Example 1, dibenzofuran (168.2 g, 1.0 moles) and 1-dodecene (168.3 g, 1.0 mole) were reacted using 15 grams of FCC Octacat USY catalyst.

EXAMPLE 4

Using the procedure in Example 1, dibenzofuran (168.2 g, 1.0 mole) and 1-hexadecene (224.4 g, 1.0 mole) were reacted using 15 grams of FCC Octacat USY catalyst.

EXAMPLE 5

Using the procedure in Example 1, dibenzofuran (168.2 g, 1.0 mole) and 1-octadecene (252 g, 1.0 mole) were reacted using 15 g of FCC Octacat USY catalyst.

EXAMPLE 6

To a stirred mixture of 1-octene (224.2 g, 2 moles), and dibenzofuran (168.2 g, 1 mole), was added 2.0 grams of anhydrous $AlCl_3$, and heated at reflux for six hours. The mixture was cooled, washed to remove inorganic materials, dried over anhydrous $MgSO_4$. Gas chromatographic analysis showed essentially complete reaction of starting material. Color of this material was >5 whereas the product of Example 1 was <2.0.

EXAMPLE 7

Using the procedure in Example 6, 1-decene, 140.27 g (1 mole) and dibenzofuran (168.2 g 1 mole) were reacted with $AlCl_3$ (2 grams) at reflux for six hours. Vacuum distillation of the washed organic mixture to 170° C. at 0.5–1.5 mm Hg resulted in the desired hydrocarbyl dibenzofuran product.

Typical properties of exemplary hydrocarbyl dibenzofuran are shown in Table 1.

TABLE 1

| Hydrocarbyl | $C_{16}$ |
|---|---|
| KV @ 100° C., cSt | 7.13 |
| VI | 77.5 |
| Pour Point (°F.) | −45 |

Performance as a Lubricant with Improved Additive Solubility

To a synthetic lubricant base stock was added 4.0 wt % of sulfurized isobutylene (as generally described by A. G. Horodysky in U.S. Pat. No. 3,703,504) and 0.5 wt % of a hindered phenolic inhibitor obtained from Ethyl Corp. as Ethyl 702. The mixture of additives was insoluble in the base stock and the sample was cloudy. To this mixture was added 21 wt % $C_{14}$ alkylated dibenzofuran. The sample was mixed; the additives completely dissolved and the mixture became clear.

Improved Thermal and Light Stability of Alkylated Dibenzofurans Over Other Lubricant Classes The results of thermal stability tests are shown below:

Thermal Stability Test

| Sample | % Viscosity Change After 72 hrs at 288° C. |
|---|---|
| $C_{16}$ Dibenzofuran | −5.8 (at 310° C.) |
| Commercial Synthetic Polyalphaolefin | |
| Sample 1 | −14.8 |
| Sample 2 | −19.4 |
| Sample 3 | −38.8 |
| Sample 4 | −60.9 |
| Sample 5 | −67.9 |
| Lube Ester | −34.2 |

Light stability was good as no color change or precipitate was observed over two months.

The use of alkylated dibenzofuran as a suitable replacement for components of current lubricant formulations is highly desirable. For example, synthetic and/or mineral based lubricant composition containing esters for improved additive solubility would be significantly improved by replacement with alkylated dibenzofuran due to its excellent thermal stability and excellent additive solubility. Alkyl dibenzofuran prepared as described herein provide excellent base stock properties and could themselves serve as the base stock in formulations for various applications, for example, applications where high temperatures are maintained.

Although the present invention has been described with preferred embodiments, it is to be understood that modifications and variations may be resorted to, without departing from the spirit and scope of this invention, as those skilled in the art will readily understand. Such variations and modifications are considered within the purview and scope of the appended claims.

We claim:

1. A process for the preparation of a high-temperature stable lubricant fluid or lubricant additive comprising catalytically monoalkylating in the presence of a synthetic zeolite catalyst having an alpha value below 100 and an olefinic alkylating agent yielding a hydrocarbyl substituent optionally containing S, N, O, P, F, or mixtures thereof, dibenzofuran, and wherein said hydrocarbyl substituent is selected from the group consisting of alkyl, alkenyl, alkynyl, arylalkyl, and aryl containing from 3 to about 500 carbons wherein the reaction temperature varies from ambient to about 350° C., the molar ratio of said olefinic alkylating agent to dibenzofuran varies from about 1:1 to about 10:1 and the amount of catalyst varies from 5 to about 100 grams of catalyst to about 1 mole of dibenzofuran.

2. The process of claim 1 wherein the catalyst is selected from the group consisting of zeolite X, Y, UHP-Y, ZSM-12, ZSM-20, ZSM-22, and MCM-22.

3. The process of claim 2 wherein the catalyst is FCC USY.

4. The process of claim 1 wherein the alkylating agent is 1-tetradecene and the catalyst is FCC USY.

5. The process of claim 1 wherein the alkylating agent is 1-dodecene and the catalyst is FCC USY.

6. The process of claim 1 wherein the alkylating agent is 1-hexadecene and the catalyst is FCC USY.

7. The process of claim 1 wherein the alkylating agent is 1-octadecene and the catalyst is FCC USY.

* * * * *